(12) United States Patent
Raa et al.

(10) Patent No.: US 8,057,809 B2
(45) Date of Patent: Nov. 15, 2011

(54) BIOACTIVE COPEPOD-COMPOSITIONS, PROCESSES FOR THE PRODUCTION THEREOF, AND USE THEREOF TO PREVENT OR TREAT HOSTS INFESTED BY PHYLOGENETICALLY SIMILAR ECTOPARASITES

(75) Inventors: Jan Raa, Oslo (NO); Gunnar Rørstad, Tromsø (NO)

(73) Assignee: Calanus AS, Tromso (NO)

(*) Notice: Subject to any disclaimer, the term of this patent is extended or adjusted under 35 U.S.C. 154(b) by 0 days.

(21) Appl. No.: 12/272,821

(22) Filed: Nov. 18, 2008

(65) Prior Publication Data

US 2009/0130149 A1    May 21, 2009

Related U.S. Application Data

(60) Provisional application No. 60/988,827, filed on Nov. 19, 2007.

(51) Int. Cl.
*A61K 39/00* (2006.01)
*A61K 39/002* (2006.01)
*A23K 1/165* (2006.01)
*A23K 1/17* (2006.01)

(52) U.S. Cl. .................. 424/265.1; 424/442

(58) Field of Classification Search .......... None
See application file for complete search history.

(56) References Cited

U.S. PATENT DOCUMENTS

| | | | | |
|---|---|---|---|---|
| 5,401,727 A * | 3/1995 | Rorstad et al. | ........ | 514/54 |
| 5,770,621 A * | 6/1998 | Braidwood et al. | ........ | 514/521 |
| 6,054,454 A * | 4/2000 | Schmid et al. | ........ | 514/229.2 |
| 6,376,650 B1 * | 4/2002 | Raa et al. | ........ | 530/343 |
| 6,538,031 B1 * | 3/2003 | Schmid | ........ | 514/595 |
| 6,747,001 B2 * | 6/2004 | Raa et al. | ........ | 514/2 |
| 6,958,385 B2 * | 10/2005 | Raa et al. | ........ | 530/343 |
| 6,982,285 B2 * | 1/2006 | Schmid | ........ | 514/595 |
| 7,358,332 B2 * | 4/2008 | Raa et al. | ........ | 530/343 |
| 2003/0068670 A1 * | 4/2003 | Raa et al. | ........ | 435/68.1 |
| 2004/0214262 A1 * | 10/2004 | Raa et al. | ........ | 435/68.1 |
| 2008/0188427 A1 * | 8/2008 | Dick et al. | ........ | 514/28 |
| 2009/0130149 A1 * | 5/2009 | Raa et al. | ........ | 424/265.1 |

FOREIGN PATENT DOCUMENTS

| EP | 466037 A2 * | 1/1992 |
|---|---|---|
| WO | WO 95/30022 * | 11/1995 |
| WO | WO 2006/010265 | 2/2006 |
| WO | WO 2007/039509 | 4/2007 |
| WO | WO 2009/067020 * | 5/2009 |

OTHER PUBLICATIONS

Leising et al, Progress in Oceanography, 2005, 67:384-405.*
Robertsen et al, J. Fish Diseases, 1990, 13:391-400.*
Krkosek et al, Science, Dec. 12, 2007, 318:1772-1775 (Erratum attached).*
Aarseth et al, Marine Ecology Progress Series, Sep. 17, 1999, No. 186, pp. 211-217 (abstract only).*
Huys et al, Molecular Phylogenetics and Evolution, 2007, 43:368-378.*
Krkosek et al, Proceedings of the Royal Society B, 2005, 272:689-696.*
Huys et al, Molecular Phylogenetics and Evolution, 2007, 43:368-378.*
Scholz, Vet. Parasitology, 1999, 84:317-335.*
Alvarez-Pellitero, Vet. Immunology and Immunopathology, 2008, 126:171-198.*
Calanus AS, 2010, 1 page.*
Prospects within Biotechnology in the Tromso region, 2010, 24 pages.*
Boxaspen et al.: "A review of the biology and genetics of sea lice", Ices Journal of Marine Science, Academic Press, vol. 63, No. 7, Jan. 8, 2006, pp. 1304-1316, XP005593174.
Costello et al.: "Ecology of sea lice parasitic on farmed and wild fish", Trends in Parasitology, Elsevier Current Trends, vol. 22, No. 10, Jan. 10, 2006, pp. 475-483, XP025230034.
J. Rpoer et al.: The immunocytochemical localisation of potential candidate vaccine antigens from the salmon louse *Lepeophtheirus salmonis* (Kroyer 1837), Aquaculture, Elsevier, vol. 132, No. 3-4, Jan. 1, 1995, pp. 221-232, XP002419574.
Marie Labus et al.: "Identification and expression of antigens from *Lepeophtheirus salmonis* for use in vaccination trials", Biochemical Society Transactions, Portland Press Ltd., GB, vol. 24, No. 2, Dec. 12, 1995, p. 254S, XP009078712.
Robert S. Raynard et al.: "Development of vaccines against sea lice", Pest Management Science, Wiley & Sons, Bognor Regis, GB, vol. 58, No. 6, Jan. 6, 2002, pp. 569-575, XP002419573.
T.H. Grayson et al: "Immunization of Atlantic salmon against the salmon louse: identification of antigens and effects on louse fecundity", Journal of Fish Biology, Elsevier, NL, vol. 47, No. SUPPL. A, Jan. 1, 1995, pp. 85-94, XO000872292.
Aderem A and RJ Ulevitch. Toll-like receptors in the induction of the innate immune response. Nature 2000; 406:782-787.
H.R. Skjoldal (ed.) 2004. The Norwegian Sea Ecosystem. Tapir Academic Press, pp. 559, ISBN 82 519 1841 3.
M. Costello 2006. Trends in Parasitology, vol. 22 No. 10, 475-483.
Z. Kabata 1979. Parasitic copepoda of British Fishes. The Royal Society. British Museum (Natural History). pp. 469, ISBN 0 903874 05 9.

* cited by examiner

*Primary Examiner* — Nita M Minnifield
(74) *Attorney, Agent, or Firm* — Christian D. Abel

(57) ABSTRACT

The present invention relates to novel compositions comprising copepods, such as marine *Calanus* species, process for the production thereof and use of said compositions in the prevention and/or treatment of ectoparasite infestations in animals. Further the invention relates to methods for prevention and/or treatment of ectoparasite infestations in aquatic animals, particularly fish.

15 Claims, No Drawings

__US 8,057,809 B2__

BIOACTIVE COPEPOD-COMPOSITIONS, PROCESSES FOR THE PRODUCTION THEREOF, AND USE THEREOF TO PREVENT OR TREAT HOSTS INFESTED BY PHYLOGENETICALLY SIMILAR ECTOPARASITES

CROSS-REFERENCE TO RELATED APPLICATIONS

This application claims the benefit under 35 USC §119 to U.S. provisional application 60/988,827, filed 19 Nov. 2007.

FIELD OF INVENTION

The present invention relates to novel compositions comprising copepods, such as marine *Calanus* species, process for the production thereof and use of said compositions in the prevention and/or treatment of ectoparasite infestations in animals. Further the invention relates to methods for prevention and/or treatment of ectoparasite infestations in aquatic animals, particularly fish.

BACKGROUND OF THE INVENTION

Ectoparasites and particularly salmon lice infest salmonids such as Atlantic salmon (*Salmo salar* L) and trout (*Salmo trutta*) in seawater, and have caused substantial economic losses in the fish farming industry in Norway, Scotland, Canada and Chile. The estimated annual losses in recent years are in the order of one billion Norwegian krone (NOK) for the salmon farming industry in Norway alone. In addition, with the expansion of the fish farming industry and the inevitable increased abundance of salmon lice in the marine environment, sea-lice infestations are being regarded as an escalating threat also to wild fish stocks. There are also reasons for being concerned about the environmental impacts of the pesticides currently used against salmon-lice, a concern creating negative attitudes in the society to the salmon farming industry. Accordingly, sea-lice infestations is not merely a severe economic problem to the fish farming industry itself, it has created reasons for grave concern about the implications it may have for coastal ecosystems and the communities where fish farming is being conducted.

Anti-parasitic drugs such as organophosphates (trichlorvos, dichlorvos and azamethiphos) and permethrins (cypermethrin and deltamethrin) have been used to bath-treat sea-lice infested salmon. Other treatments include use of chitin synthesis inhibitors such a diflubenzuron and teflubenzuron and more recently the anti-parasitic drug emamectin benzoate, administered in the feed. Due to the inevitable process of resistance development against chemically synthesized pesticides, these compounds will most probably gradually lose their antiparasitic efficacy. It is generally accepted that such chemotherapeutic treatments are not satisfactory, both with regard to environmental acceptability and from an efficacy point of view. Hence, alternative treatments and prevention strategies are urgently needed. (M. Costello 2006. *Trends in Parasitology*, Vol. 22 No. 10, 475-483).

The use of hydrogen-peroxide against sea-lice is a notable idea tried out in practice for some years. Hydrogen peroxide will be split by catalase and cause formation of oxygen bubbles inside the sea-lice. Due to the increased buoyancy caused by these bubbles, the sea-lice will be forced to detach from the skin and float to the water surface. The method is very stressful for the fish, however, and hydrogen peroxide does not kill the lice—they may settle again. Due to practical difficulties and variable efficacy results, the method is not in widespread use.

Wrasse is a predator fish biologically specialized to feed on salmon-lice they pick off salmon skin. The use in practice of this biological principle is an attractive and ecologically sound method of sea-lice control in salmon farms, tried out in Norway during the last 10-15 years. However, there are notable limitations to large-scale implementation of the method. The wrasse fish used so far do not survive winter conditions in salmon farms, the size of the predator fish population must be adjusted according to the size of the growing salmon, and the biggest salmon swim too fast for the smaller size wrasse fishes to succeed in picking lice.

U.S. Pat. No. 5,401,727 disclose a process for stimulating the immune system of aquatic animals of the class Osteichthyes and subphylum Crustacea comprising administering an effective amount of a yeast cell wall glucan composed of glucopyranose units linked by predominantly beta-1,3 glucosidic bonds, having at least one branch therefrom of glucopyranose units linked by beta-1,6 glycosidic bonds. Additionally the invention provides a process for enhancing the effect of vaccines by administering an effective amount of the described yeast cell wall glucan along with vaccine antigens. Further this invention also provides a process of obtaining a glucan particularly effective for stimulating the immune system of aquatic animals of the class Osteichthyes and subphylum Crustacea.

Most attention in recent years has been paid to mobilizing immune mechanisms to render the fish more resistant to lice infestation. Two principles have been in focus, the first is to enhance innate immune mechanisms by known immune stimulants such as beta-1,3/1,6-glucan, the second is to mobilize adaptive immunity in the fish by injecting vaccines comprising unique antigens present in the particular sea-lice strains infesting farmed salmon. Both strategies are promising, but the use of beta-1,3/1,6-glucan is apparently closer to being implemented in commercial scale than the vaccination strategy, as commented on below.

When added to salmon feed, MACROGUARD® (an immune modulating beta-1,3/1,6-glucan) induces notable protection against salmon-lice infestation (Fish Farming International, July 2004, Vol. 34, No. 7, page 3), most likely by enhancing innate immune mechanisms in the skin and mucosa of the fish. Such mechanisms may include mucous immunoglobulins, lysozyme, complement factors and immune cells that guard tissue surfaces and attack intruding parasites. It is well known among those skilled in the art that beta-1,3/1,6-glucan triggers defence reactions by interacting with Toll-like receptors (TLRs) and with the highly specific beta-1,3/1,6-glucan receptor designated dectin. Beta-1,3/1,6-glucan is one out of many microbial structures recognized by so-called Pattern Recognition Receptors (PRRs) present in immune cells of fish and higher animals. The PRRs that recognize the beta-1,3/1,6-glucan structure have during evolution been involved in dealing with fungal intruders and in eliciting an adequate response to such infections. But activation of the PRRs specific for beta-1,3/1,6-glucan, although specifically "designed" by Nature to cope with fungal infections, also give rise to enhanced protection against virus and bacteria—and against parasites. There are at least 9 different TLRs on immune cells, designed to recognize and respond to 9 different unique bacterial and viral structures (Aderem A and RJ Ulevitch. Toll-like receptors in the induction of the innate immune response. Nature 2000; 406:782-787). However, no specific TLR for parasite structures has hitherto been found.

The fact that only one commercial vaccine exists against an ectoparasite (the cattle tick vaccine) is a reflection of the underlying difficulties associated with successful parasite protection by the adaptive immune system. The commercial tick vaccine comprises a concealed antigen that induces the production of antibodies interfering with the ticks' ability to digest blood. A corresponding strategy has been followed in Norway in research-based attempts to develop a salmon-lice vaccine. It has been demonstrated that vaccination with a concealed antigen from salmon lice induces production of antibodies that end up in the digestive organ of blood sucking salmon-lice, Challenge experiments with salmon-lice of the same type as that used in the vaccine formulation (antigens present in female salmon lice), have demonstrated that these antibodies indeed have a protective effect. The results are therefore promising, although the vaccination projects using purified salmon-lice specific antigens are still at a research stage. When new vaccine candidates targeting vital functions in sea-lice have been found, it remains to produce such vaccines commercially. If such vaccines are to be based on concealed antigens present in salmon-lice, it will take time to develop them because molecular biological screening of genes coding for the most promising targets needs to be carried out first. While waiting for the eventual great breakthrough in parasite vaccine development, every attempt should be made to combine principles that contribute to reducing the salmon louse problem in the fish farming industry.

SUMMARY OF THE INVENTION

The present invention provides bioactive compositions comprising a copepod, processes for the production thereof, and use of said compositions for the immunization of hosts against ectoparasites which have phylogenctic and hence genetic resemblance to copepods. The invention provides compositions comprising copepods of *Calanus* species and methods for use thereof for the immunization of aquatic animals, particularly fish, against ectoparasites. A composition comprising the copepod *Calanus finmarchicus* and a method for the immunization of fish against sea lice such as *Lepeophtheirus salmonis, Caligus elongatus* and *Caligus rogercresseyi* is also provided.

DESCRIPTION OF THE INVENTION

The invention comprises copepod compositions that enhance innate and adaptive immune defence mechanisms involved in the rejection of parasites.

The invention may also be applied to prevent or treat ectoparasite infestations in host animals. The expression "host animals" is meant to include any fish species as well as in warm-blooded animals.

To appreciate the uniqueness and novelty of the present invention, one has to understand the infection biology of sea-lice, its ecological features and phylogenetic relationship to other copepods, in particular the relationship to *Calanus finmarchicus* living in the same marine ecosystem as sea-lice do.

The sea-louse e.g. salmon louse starts its parasitic life by attaching to skin surface while it is in the so-called copepodite stage, one of the early stages in its life cycle. Of some reason it does not attach to gills, except on salmon living under experimental conditions in tank systems. When attached to the fish skin the salmon louse uses its rasping mouthparts as mechanical devices for penetration through the mucous and into the underlying tissues, where it finds available nutrients for growth and where it gradually develops into a bloodsucking parasite. The infestation is not only the result of a mechanical rasping process, but may involve enzymatic activities that help opening up tissue structures and facilitating leakage of nutrients the parasite needs. As a result the fish suffer from osmo-regulatory problems, epithelium damages, wounds, bleeding and secondary infections, resulting in reduced growth and high mortalities.

Successful parasitism depends on the ability of the parasite to avoid a counterattack by the host's immune system—it must "sneak" unnoticed into the host and find its nutrients without provoking immune defence reactions. This ability of a parasite to escape detection by the host's immune system can be the result of mechanisms whereby the parasite suppresses immune responses in the host and/or of an ecological adaptation whereby the parasite exposes antigens which do not elicit strong and protective immune responses by the host. These may be the reasons why injection vaccines based on crude preparations of sea-lice or based on unique antigens (i.e. chemical structures) from the sea-lice, have had limited success.

An alternative strategy for developing vaccines against ectoparasites such as salmon-lice may be to circumvent the mechanisms involved in biological adaptation between host and parasite and look for "good" antigens that are not identical to, but resemble, the parasite antigens. If antibodies against such resembling antigens also recognize antigens present in the parasite, it could be speculated that they could provide protection. Such alternative "cross-protecting" vaccines could be administered by injection, like most other vaccines are. However, since injected antigens give rise to specific antibodies primarily in the blood, the salmon-lice will not encounter these antibodies before they have developed into the blood sucking stage. Therefore, it seems to be a better strategy to find ways to elicit production of protective antibodies that are secreted into the skin and skin mucous, where such antibodies might interact with the attachment structures on the salmon-louse, interfering with its very first steps in the infestation process and inhibiting its progression through the skin tissues into the blood.

Sea-lice causing problems in salmon farms have a host base also in wild stocks of non-salmonids, and salmon and trout may even be their secondary hosts (M. Costello 2006. *Trends in Parasitology*, Vol. 22 No. 10, 475-483). A general feature of parasitic copepods is accordingly their low degree of host specificity, indicating that their infestation mechanisms are not too intricate and not uniquely designed for one particular host. Targeting very unique structures on the sea-lice by inducing production in the fish of antibodies that are highly specific to those structures is therefore not necessarily the most rewarding strategy.

It has now surprisingly been found that there are immunogenic structures common to parasitic and free-living non-parasitic copepods, such as *Calanus* species, e.g. *Calanus finmarchicus*. Such common structures elicit production of antibody and/or other protective principles by the fish. By exposing the fish to compositions comprising the parasitic copepod and/or other non-parasitic copepods cross protection against parasitic copepods is obtained.

Sea lice (order Siphonostomatoida) are widespread marine parasitic copepods. More than 290 species, belonging to the genera *Lepeophtheirus* and *Caligus* (family Caligidae), have been described. The economically most detrimental species to fish farming are *Lepeophtheirus salmonis, Caligus elongatis* and *Caligus rogercresseyi*. Although mainly Atlantic salmon (*Salmo salar* L.) and sea-living trout are more severely affected, salmon lice have been recorded on at least 12 species in the genera *Salmo* (North-Atlantic salmon and trout), *Salvelinus* (trout and charr), and *Oncorhynchus* (Pacific salmon).

The evolution of copepods started during the geological time periods Silur-Devon and/or Jura Kritt. All copepod groups of today have developed from a common bottom living ancestor (Z. Kabata 1979. *Parasitic copepoda of British Fishes*. The Royal Society. British Museum (Natural History). Pp 469, ISBN 0 903874 05 9). From this ancestor the current free-living copepods have developed, including *Calanus finmarchicus*, and also the copepods that have developed a parasitic feeding behaviour, such as sea-lice species. Their common ancestry reveals itself in particular by the fact that that copepods belonging to various orders and genera have very similar and conserved early ontogenic stages, particularly in the so-called nauplii- and copepodite-stages.

*Calanus* is a genus of marine, free-living (planktonic) copepods found in large amounts over wide oceanic and coastal areas. In the North Atlantic, at least 4 species have been described, including *C. finmarchicus, C. glacialis, C. hypeboreus* and *C. helgolandicus*. The species *Calanus finmarchicus* for instance the dominant copepod in the Nordic Seas (the Norwegian Sea and adjacent seas) both by number and biomass. *C. finmarchicus* is a key species constituting the main link between primary production of plant plankton and fish and mammalian species higher in the food chains in this vast area. It is a major energy source in the North Atlantic food-web and an essential food-source during one or several life stages for a wide range of fish and animal species in these waters (H. R. Skjoldal (ed.) 2004. *The Norwegian Sea Ecosystem*. Tapir Academic Press. Pp 559, ISBN 82 519 1841 3).

*Calanus*-species are naturally available as a food source to a multitude of wild fish species, including salmonids, when they are available in their nauplii- and copepodite-stages in the upper waters in spring and summer. When growing under aquaculture conditions, however, salmon, trout and other species have been deprived from this natural food organism to which they are evolutionary adapted. The present invention is based on compositions comprising *Calanus* spp. such as *C. finmarchicus*, which are harvested from oceanic and coastal waters during their copepodite-stages. Moreover, the present invention is based on the fact that sea-lice of the genera *Caligus* and *Lepeophtheirus* are infecting fishes during their copepodite stages, which are phylogenetically very similar to that of *Calanus*. Thus, it is envisioned that a composition comprising *Calanus*, either alone or in combination with one or more adjuvant, may be applied to enhance the innate and adaptive mucosal immunity of fishes, so that they will enhance their ability to counteract sea-lice infestations.

It is envisaged that *Calanus finmarchicus* may elicit innate defence as well as specific immune responses. Throughout evolution animals have developed mechanisms for early detection of chemical structures (PRRs) unique for infectious micro-organisms enabling the immune system to respond adequately and early enough to immobilize and destroy the infectious microorganism. Although no PRRs hitherto have been described for structures present in parasites, it does not mean that such structures do not exist. On the contrary, from an ecological point of view it is quite likely that fish and other animals throughout evolution have developed mechanisms for early detection of, and immediate response to, intruding parasites. It is therefore an implicit part of the present invention that the bioactive effects of compositions made of *Calanus* species, are caused by a parasite specific PRR interacting with a signal molecule present in *Calanus* sp.

Compositions comprising *Calanus*-copepodites may be in the form of unprocessed, fresh or frozen stored, or be in the form of a crude powders made by any conventional drying process, including the traditional fish-meal process. It may also include de-oiled, partially or wholly purified compositions, moist or dry, and hydrolysed *Calanus*-copepodites. The compositions may either be given orally as part of feed-formulations or coated thereon, or as an immersion or bath-treatment of the fish, either alone or in combinations with one or more adjuvant which are known to enhance the innate immunity of animals, such as e.g. beta-glucans, peptidoglycans, nucleotides, oligonucleotides or mixtures thereof either synthesized or produced from yeasts, fungi and bacteria.

The innate immune system, in which Toll-like receptors are believed to play an important role, defends the host from infestation by foreign organisms like parasites in a non-specific manner. The recognition and response of the innate immune system to pathogens is generic and provide an immediate defence.

An overall general immune enhancement of hosts against ectoparasites which have phylogenetic and hence genetic resemblance to copepods can be obtained by injection of a purified composition comprising *Calanus*. Particularly a general immune enhancement in fish against sea lice such as *Lepeophtheirus salmonis, Caligus elongatus* and *Caligus rogercresseyi* can be obtained by injection of a purified composition comprising *Calanus*, preferably *Calanus finmarchicus*. Such compositions for administration by injection may be administered alone or optionally with one or more adjuvant and in an amount of 0.001-10 mg *Calanus* per kg fish, preferably 0.01-1 mg *Calanus* per kg fish.

The composition according to the invention comprises *Calanus*, particularly *Calanus* of the species *Calanus finmarchicus*. The ectoparasites against which the immunization is directed belong to the genera *Lepeophtheirus* and/or *Caligus*, and particularly to the group *Lepeophtheirus salmonis, Caligus elongatus* and *Caligus rogercresseyi*. The host animal to receive the composition is any animal exposed to ectoparasites and particularly fish, and fish particularly belonging to the genera *Salmo* (North-Atlantic salmon and trout), *Salvelinus* (trout and charr), and/or *Oncorhynchus* (Pacific salmon), and most particularly the fish is *Salmo salar* L.

In one embodiment of the present invention a composition comprising *Calanus*, for the immunization of fish, particularly Salmonidae, against sea-lice is provided. The composition comprises a bioactive crude powder made by a traditional fish-meal process, or a dried or moist partially or wholly purified and de-oiled concentrate of hydrolysed *Calanus*. The compositions may either be given orally as part of feed-formulations or coated thereon, in an amount of 0.1-100 g per kg feed, preferably 0.1-10 g per kg feed, more preferably 0.5-5 g per kg feed.

In another embodiment of the present invention a method for the immunization of Salmonidae against sea lice is provided where the Salmonidae is fed *Calanus*. The feeding with a fodder composition comprising *Calanus* is commenced 0-12 weeks prior to the time when the fish is expected to become exposed to infecting sea-lice. The feeding with *Calanus* may proceed until the earliest of the time when the fish is not longer exposed or infested.

In another embodiment of the present invention a method for the immunization of Salmonidae against sea-lice is provided where the Salmonidae is immersion treated in a bath comprising *Calanus* in an amount of 0.1-100 g per L, preferably 1-10 g per L, more preferably 1-5 g per L of water for 1-60 minutes, said water bath preferably being oxygenated and having a water temperature of 5-15° C.

In an embodiment of the present invention a composition for administration by injection is provided and administered in an amount of 0.001-10 mg *Calanus* per kg fish, preferably 0.01-1 mg *Calanus* per kg fish.

In a further embodiment a method for the immunization of animals is provided wherein a composition comprising an amount of 0.001-10 mg *Calanus* per kg fish, preferably 0.01-1 mg *Calanus* per kg fish is administered by injection.

In yet another embodiment of the present invention a method for the immunization of Salmonidae against sea lice is provided wherein a composition comprising *Calanus*, either given orally, by immersion or injected, is combined with one or more adjuvant. Such adjuvant may be a substance known to enhance the innate or adaptive immunity of the host, such as e.g. beta-glucans, peptidoglycans, nucleotides, oligonucleotides or mixtures thereof either synthesized or produced from yeasts, fungi and bacteria.

The adjuvant may be given via the same or a different route than the *Calanus* comprising composition.

In one particular embodiment of the present invention a composition comprising *Calanus finmarchicus*, for the immunization of Salmonidae, particularly Atlantic salmon, against sea-lice is provided. The composition comprises a bioactive crude powder made by a traditional fish-meal process, or a dried or moist partially purified and de-oiled concentrate of hydrolysed *Calanus finmarchicus*. The compositions may either be given orally as part of feed-formulations or coated thereon, in an amount of 0.1-100 g per kg feed, preferably 0.1-10 g per kg feed, more preferably 0.5-5 g per kg feed.

In another particular embodiment of the present invention a method for the immunization of Atlantic salmon against sea-lice is provided where the Atlantic salmon is fed *Calanus finmarchicus*. The feeding with a fodder composition comprising *Calanus finmarchicus* is commenced 0-12 weeks prior to the time when the fish is expected to become exposed to infecting sea-lice, and the feeding with said *Calanus* may be proceeded until the earliest of the time when the fish is no longer exposed or infested.

In another particular embodiment of the present invention a method for the immunization of Atlantic salmon against sea-lice is provided where the salmon is immersion treated in a bath comprising *Calanus finmarchicus* in an amount of 0.1-100 g per L, preferably 1-10 g per L, more preferably 1-5 g per L of water for 1-60 minutes, said water bath preferably being oxygenated and having a water temperature of 5-15° C.

In yet another particular embodiment of the present invention a method for the immunization of Atlantic salmon against sea lice is provided wherein a composition comprising *Calanus finmarchicus*, either given orally, by immersion or injection, is combined with one or more adjuvant. Such adjuvant may be a substance known to enhance the innate or adaptive immunity of the host, such as e.g. beta-glucans, peptidoglycans, nucleotides, oligonucleotides or mixtures thereof either synthesized or produced from yeasts, fungi and bacteria.

The adjuvant may be given via the same or a different route than the *Calanus finmarchicus* comprising composition.

A crude powder or meal comprising *Calanus*-copepodite is manufactured from catch of *Calanus* by conventional methods used in the manufacturing of fish meal using suitable processing conditions. The composition comprises a bioactive crude powder made by a traditional fish-meal process, or a dried or moist partially or wholly purified and de-oiled concentrate of hydrolysed *Calanus*. The feed composition according to the present invention is manufactured by mixing or top-coating such meal of *Calanus* in conventional fodder compositions for fish.

The composition according to the present invention is suitable for use for the immunisation of a host animal against ectoparasites which are phylogenetically and immunologically similar to *Calanus*. Particularly the composition is suitable for the immunisation of fish in the genera *Salmo* (North-Atlantic salmon and trout), *Salvelinus* (trout and charr), and/or *Oncorhynchus* (Pacific salmon) against ectoparasites belonging to the group *Lepeophtheirus salmonis, Caligus elongatus* and *Caligus rogercresseyi*.

The following non-limiting examples further illustrate certain embodiments of the invention.

EXAMPLES

Example 1

Controlled Challenge Trial

Five different groups of 15 Atlantic salmon were kept in 5 different tanks supplied with seawater of temperature of 14-16° C. Five different diets, one for each group, were produced as follows, using a standard diet as common basis: A: Control (no *Calanus* Powder), B: 1 g *Calanus* Powder per kg feed, C: 5 g *Calanus* Powder per kg feed, D: 10 g *Calanus* Powder per kg feed, and E: 1 g *Calanus* Powder per kg feed top-coated. Each diet was fed for 8 weeks, after which 15 fish from each group were marked and combined in tanks where they were challenged by the Chilean copepodite sealice *Caligus rogercresseyi*, cultured in the laboratory at Universidad Austral de Chile. After challenge, all fish were fed the control diet. Eight days after challenge the number of sealice on each fish were counted. The results were as shown in Table 1 below:

TABLE 1

| Feed (group): | Average number of lice per fish (n = 15): |
|---|---|
| A | 12.9 |
| B | 8.2 |
| C | 13.2 |
| D | 11.3 |
| E | 8.1 |

The results indicate that *Calanus* Powder indeed has immune stimulating property, despite the fact that the challenge pressure in this case may have been too high. Moreover, the results show that 1 gram *Calanus* Powder per kg feed, either top-coated or mixed into the feed, appears to be closer to optimum level than 5 or 10 grams/kg. The dose/response effect of *Calanus* Powder, as shown in Table 1, is typical for immune stimulants. A common feature of such substances is that their immune stimulatory effect is evident within certain concentration ranges and disappears, or become negative, at high concentrations.

Example 2

Field Trials

Atlantic salmon in Norwegian commercial fish farms were fed on a standard diet (Feed A) and on the same diet added *Calanus* Powder in an amount of 10 g/kg feed (Feed B). Feeding on the experimental diets began 2 weeks before transfer of the fish from freshwater to floating sea-cages, and lasted for 6 weeks (Site 1) and 8 weeks (Site 2) before monitoring of sealice infestations (*Lepeophtheirus salmonis*) by randomly sampling 60 salmon from each group (20 salmon per cage, 3 cages per group). The results from the two different sites are shown in Table 2.

TABLE 2

| | Average number of sealice per fish (n = 60): | |
|---|---|---|
| | Site 1 | Site 2: |
| Feed A: | 0.18 | 0.48 |
| Feed B: | 0.03 | 0.10 |

The results indicate a prophylactic effect of *Calanus* Powder even under field conditions, and despite the fact that the concentration of *Calanus* Powder in this case was as high as 10 g/kg feed.

The invention claimed is:

1. Method for the immunization of host animals against ectoparasites belonging to the group *Lepeophtheirus salmonis, Caligus elongatus* and *Caligus rogercressey* comprising the step of feeding the host animal with a composition comprising *Calanus*, wherein said host animals are fish.

2. Method according to claim 1 wherein said host animal is a fish is in the genera *Salmo* (North-Atlantic salmon and trout), *Salvelinus* (trout and charr), and/or *Oncorhynchus* (Pacific salmon).

3. Method according to claim 2 wherein said fish is *Salmo salar* L.

4. Method according to claim 1 wherein the comprised *Calanus* species is *Calanus finmarchicus*.

5. Method according to claim 1 wherein the feeding with said *Calanus* comprising composition starts 0-12 weeks prior to exposure to said ectoparasites.

6. Method for the immunization of host animals against ectoparasites belonging to the group *Lepeophtheirus salmonis, Caligus elongatus* and *Caligus rogercresseyi*, comprising the step of exposing the host animal to a composition comprising *Calanus* by immersing the host animal in a bath comprising the composition, wherein said host animals are fish.

7. Method according to claim 5 wherein said exposure to said *Calanus* comprising composition starts 0-12 weeks prior to exposure to said ectoparasites.

8. Method according to claim 5 wherein said host animal is immersed in said bath for 1-60 minutes.

9. Method according to claim 5 wherein bath is being oxygenated and having a temperature of 5-15° C.

10. Method for the immunization of fish against ectoparasites, belonging to the group *Lepeophtheirus salmonis, Caligus elongatus* and *Caligus rogercressey*, wherein said fish are immunized by injection with a composition comprising *Calanus* in an amount of 0.001-10 mg *Calanus* per kg fish.

11. Method according to claim 10 wherein said fish are injected with a composition comprising *Calanus* in an amount of 0.01-1 mg *Calanus* per kg fish.

12. Method according to claim 1 wherein the composition comprising *Calanus* is a crude powder.

13. Method according to claim 1 wherein the composition comprises unprocessed *Calanus*.

14. Method according to claim 1 wherein the composition comprising *Calanus* is a dried, purified and de-oiled concentrate of hydrolysed *Calanus*.

15. Method according to claim 1 wherein the composition comprising *Calanus* is a moist, purified and de-oiled concentrate of hydrolysed *Calanus*.

* * * * *